Figure 1:
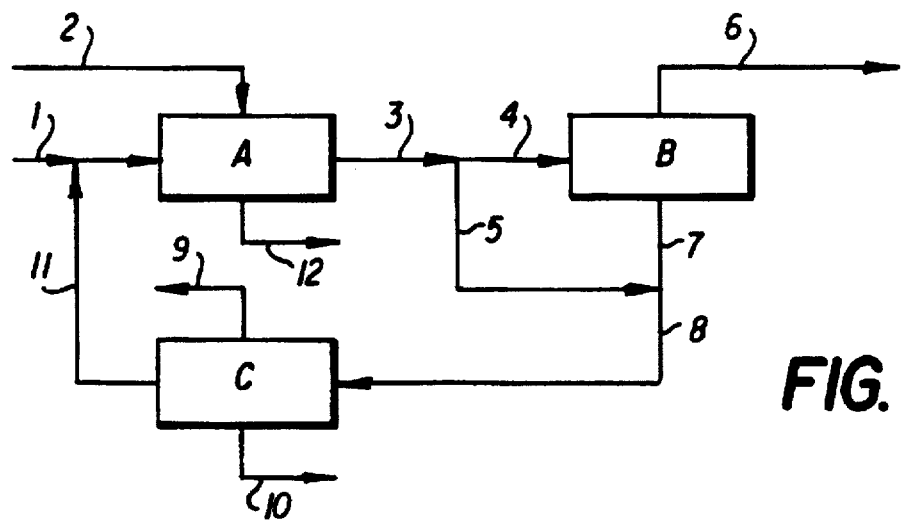

United States Patent
Trotta et al.

Patent Number: 5,672,771
Date of Patent: Sep. 30, 1997

[54] INTEGRATED PROCESS FOR THE PRODUCTION OF TER-AMYL ALKYL ETHERS

[75] Inventors: Roberto Trotta, Milan; Gianni Donati, Rho; Renato Paludetto, Pioltello; Paolo Chiudaroli, S. Donato Milanese, all of Italy

[73] Assignees: Enichem S.p.A., Milan; Snamprogetti S.p.A., S. Donati Milanese

[21] Appl. No.: 546,989

[22] Filed: Oct. 23, 1995

[30] Foreign Application Priority Data

Dec. 21, 1994 [IT] Italy ............... MI94A2589

[51] Int. Cl.$^6$ .................................. C07C 41/32
[52] U.S. Cl. ........................................ 568/697
[58] Field of Search ............................. 568/697

[56] References Cited

U.S. PATENT DOCUMENTS 5,254,748  10/1993  Hensley ................. 568/697
5,300,696  4/1994   Luebke et al. ......... 568/697

FOREIGN PATENT DOCUMENTS 0667329  1/1995  European Pat. Off. .

*Primary Examiner*—Joseph Conrad
*Attorney, Agent, or Firm*—Watson Cole Stevens Davis, P.L.L.C.

[57] ABSTRACT

Integrated process for the production of ter-amyl alkyl ethers which comprises the feeding of a $C_5$ hydrocarbon stream to an etherification reactor and the recycling of the remaining stream to the same reactor, after treatment in an isomerization section to convert linear pentenes into reactive isoamylenes. An absorption section on molecular sieves is inserted between the etherification reactor and the isomerization section to eliminate inert hydrocarbons, basically i-pentane and n-pentane.

15 Claims, 1 Drawing Sheet

INTEGRATED PROCESS FOR THE PRODUCTION OF TER-AMYL ALKYL ETHERS

The present invention relates to an integrated process for the production of ter-amyl alkyl ethers.

More specifically, the present invention relates to an integrated process for the production of ter-amyl methyl ether (TAME) or ter-amyl ethyl ether (TAEE).

Even more specifically, the present invention relates to the maximization of the use of the pentene fraction in an integrated cycle for the production of TAME or TAEE.

Processes for the production of ter-amyl alkyl ethers are known in the art, consisting in reacting 2-methyl-1-butene or 2-methyl-2-butene (reactive isoamylenes), contained in $C_5$ hydrocarbon streams of different origins, in particular in streams coming from steam cracking or catalytic cracking plants, with an alcohol, preferably selected from methanol and ethanol. U.S. Pat. No. 3,979,461, for example, describes a process for the preparation of TAME wherein the isoamylenes, contained in $C_5$ streams are reacted with methanol in the presence of an acid ion-exchange resin.

The known processes allow a high conversion of the reactive isoamylenes and leave the other components, in particular pentene-1 and pentene-2, cis and trans, and 3-methyl-1-butene which must be recovered for evaluation, practically unvaried.

At present the most widely used form for having the best use of these streams consists in inserting them into the gasoline production cycle after hydrogenation of the unsaturated hydrocarbons.

The Applicants have now found a further form of best use of these streams based on the recovery of the pentenes, their skeleton isomerization and recycling to the etherification unit.

In particular the Applicants have found a process for the production of ter-amyl alkyl ethers in connection with a cycle for the best use of the residual components still present in the $C_5$ stream leaving the etherification reactor. According to this process, the $C_5$ stream, after synthesis and separation from the teramyl ether, is sent to an isomerization unit, for conversion of the pentene-1, pentenes-2, cis and trans, and 3-methyl-1-butene to reactive isoamylenes, and is recycled to the synthesis section of the ter-amyl alkyl ether. As there is an undesired accumulation of inert products, basically consisting of saturated hydrocarbons such as n-pentane and isopentane, in an integrated system of this kind, a separation section with molecular sieves has been inserted between the etherification and isomerization sections for the separation of the pentanes from the pentenes and recovery of the pentenes. More specifically, the separation is obtained by means of a selective absorption of the olefins on zeolites.

The olefins thus absorbed can be recovered by desorption and recycled to the isomerization section. This result, however, can be obtained if the separation on molecular sieves is carried out with the stream in the vapour phase, as operating in a liquid phase produces unsatisfactory results.

The present invention therefore relates to an integrated process for the production of ter-amyl alkyl ethers which comprises:

a) feeding a $C_5$ hydrocarbon stream, basically consisting of 2-methyl-1-butene and/or 2-methyl-2-butene (reactive isoamylenes), linear pentenes, 3-methyl-1-butene and pentanes to a synthesis section of ter-amyl alkyl ethers together with a stream consisting of an aliphatic alcohol;

b) separating the ether produced and the possible non-reacted alcohol from the hydrocarbon stream;

c) sending the remaining hydrocarbon stream, in a vapour phase, or a fraction thereof, to a separation section with molecular sieves for the separation of the pentanes from the pentenes and recovery of the pentenes;

d) sending the hydrocarbon stream containing the recovered pentenes, together with the possible non-fed fraction in step (c), to a skeleton isomerization section for the transformation of the linear pentenes to reactive isoamylenes;

e) recycling the isomerized stream to the synthesis reactor of the ter-amyl alkyl ether after mixing with the charged $C_5$ hydrocarbon stream.

Alternatively, the charged $C_5$ hydrocarbon stream can have a low content of reactive isoamylenes, if this comes, for example, from a plant for the synthesis of pre-existing ter-amyl alkyl ethers. In this case the $C_5$ stream can be fed directly to the isomerization section and then to the etherification section. After separation of the ether produced, the outlet stream is sent for separation of the saturated hydrocarbons, recycling the released pentene fraction to the isomerization section.

A further integrated process for the production of ter-amyl alkyl ethers can comprise:

a) feeding a $C_5$ hydrocarbon stream, basically consisting of 2-methyl-1-butene and/or 2-methyl-2-butene (reactive isoamylenes), linear pentenes, 3-methyl-1-butene and pentanes to a synthesis section of ter-amyl alkyl ethers together with a stream consisting of an aliphatic alcohol;

b) separating the ether produced and the possible non-reacted alcohol from the hydrocarbon stream;

c) sending the remaining hydrocarbon stream to a skeleton isomerization section of the linear pentenes to transform the linear pentenes to reactive isoamylenes;

d) sending the isomerized hydrocarbon stream leaving step (c), in a vapour phase, or a fraction thereof, to a molecular sieve separation section for the separation of the pentanes from the pentenes and the recovery of the pentenes;

e) recycling the isomerized stream, containing the recovered pentenes, together with the possible fraction not fed in step (d), to the synthesis reactor of the ter-amyl alkyl ether after mixing with the $C_5$ hydrocarbon stream to be charged.

Also in this further embodiment of the process of the present invention, the $C_5$ hydrocarbon stream to be charged can have a low content of reactive isoamylenes as it comes from a plant for the synthesis of pre-existing ter-amyl alkyl ethers. In this case the $C_5$ stream can be fed directly to the isomerization section, and then, to the molecular sieve separation section.

The $C_5$ hydrocarbon stream which is used in the process of the present invention basically consists of isopentane, isoamylenes, n-pentane, pentene-1, pentene-2, trans or cis, and, possibly, $C_4$ or $C_6$ hydrocarbons and is substantially free of isoprene and cyclopentadiene as it comes from a hydrogenation unit of these.

In particular, a $C_5$ stream, in addition to a quantity of $C_4$ and $C_6$ of between, for example, 0 and 20% by weight, can comprise about: 1–70% by weight of isopentane; 0.5–30% by weight of n-pentane; 0.1–30% by weight of cyclopentane; 0.5–20% by weight of linear pentenes, taken individually; 0.1–30% by weight of cyclopentene; 0.1–10% by weight of 3-methyl-1-butene; 0.5–30% by weight of, 2-methyl-1-butene; 0.5–50% by weight of 2-methyl-2-butene; 0–2% by weight for each diolefin taken individually.

Any aliphatic alcohol can be used in the process of the present invention even if methyl and ethyl alcohol are preferred to produce ter-amyl methyl ether (TAME) and ter-amyl ethyl ether (TAEE) respectively.

The etherification reaction is carried out, preferably, in a liquid phase in the presence of an acid catalyst under the traditional operating conditions. As an alternative to the traditional technologies the ether can be synthesized by means of a column-reactor, according to the catalytic distillation principle described, for example, in U.S. Pat. No. 4,475,005 or in European patent application 470.655.

The hydrocarbon stream, coming from the etherification unit, is sent to a separation section to recover the ether produced and the possible non-reacted alcohol. The separation of the residual $C_5$ fraction from the ether is carried out in a normal distillation column from whose bottom a product is separated consisting of ether and possible $C_6^+$ hydrocarbons. At the top of the column the $C_5$ hydrocarbons are recovered with the non-reacted alcohol. The alcohol is then removed with the known methods, for example by extraction with water.

The residual $C_5$ fraction, without ether and alcohol, or a fraction of more than 5% by weight of the total stream available, is sent to a molecular sieve separation section to eliminate the inert products, consisting of aliphatic hydrocarbons, basically n-pentane and isopentane.

Any molecular sieve of the zeolitic type capable of having selectivity with respect to the double olefinic bond can be used in the process of the present invention. For example, compounds can be used corresponding to those having the general formula (I):

$$(Cat_{2/n}O)_xMe_2O_3(SiO_2)_y \qquad (I)$$

wherein:

Cat represents a cation of valence "n", inter-changeable with calcium (Ca), such as sodium, lithium, potassium, magnesium, etc;

x is a number between 0.7 and 1.5;

Me represents boron or aluminium; and y is a number between 0.8 and 200, preferably between 1.3 and 4.

Zeolites of the X and Y type are preferred with a particle size of between 0.1 and 3 mm. These zeolites allow selectivity ratios olefins/paraffins to be obtained of between 3 and 12, the selectivity being defined as:

$$S = \frac{\Gamma_o/P_o}{\Gamma_p/P_p}$$

wherein $\Gamma_o$ and $\Gamma_p$ are the adsorbed molar quantities of olefins (o) and paraffins (p) in equilibrium with the respective partial pressures $P_o$ and $P_p$ in the vapour.

The separation (adsorption) of the aliphatic hydrocarbons is carried out in the vapour phase at a temperature of between 20° and 180° C., preferably between 50° and 140° C., and a pressure of between 1 and 10 absolute bars, preferably between 1 and 5. To guarantee continuity of the process of the present invention, it is preferable to use a system of at least two sections arranged parallel to each other so that when one section is in the adsorption phase, the other is in the desorption phase. The latter is carried out by elution of the olefins adsorbed on the molecular sieves with a desorbing agent having a boiling point higher than that of the hydrocarbons treated, for example with aliphatic hydrocarbons such as hexane, heptane, octane, etc., in the vapour phase and subsequent rectification of the mixture obtained to recover the olefins.

The process of the present invention enables the production of an aliphatic hydrocarbon stream which is practically without olefins or with a content of olefins of up to 5% by weight.

The olefinic stream which leaves the molecular sieve separation section, basically consisting of the fraction of residual pentanes, pentene-1 and pentene-2, cis and trans, and 3-methyl-1-butene, is sent to the isomerization section for the conversion of the pentene-1 and pentene-2, cis and trans, and 3-methyl-1-butene to reactive isoamylenes.

The isomerization reaction can be carried out, for example, by the process described in U.S. Pat. No. 4,038,337 using, as catalyst, a product based on silicized alimina described in U.S. Pat. Nos. 4,013,589 and 4,013,590 or using zeolitic catalyts such as those, for example, described in European patent applications publications 523.838 and 501.577.

At the outlet of the isomerization section a stream rich in reactive isoamylenes is obtained, which can be recycled to the synthesis of ter-amyl alkyl ether.

The integrated process for the production of teramyl alkyl ethers of the present invention can be better illustrated with reference to the block schemes of FIGS. 1 and 2 which represent two exemplifying but not limiting forms of the embodiment, and FIG. 3 which represents an illustrative form of the single molecular sieve separation section.

With reference to FIG. 1, A, B and C represent respectively the synthesis section of ter-amyl alkyl ether, the molecular sieve separation section of the aliphatic hydrocarbons and the skeleton isomerization section. The feeding stream, consisting of the sum of the $C_5$ hydrocarbon fraction (1) and the recycled fraction (11) coming from the isomerization unit C, is sent to the synthesis section A, together with the aliphatic alcohol (2). When the ether produced (12) has been recovered, by means of conventional systems not shown in the figure, the residual fraction (3) is sent, either totally or partially, to the separation section B. If there is a partial separation, part of the above residual fraction by-passes the separation section B (5).

The stream (7), coming from the separation section B, basically consisting of pentene-1 and pentene-2, cis and trans, 3-methyl-1-butene and residual pentanes rejoins the stream (5) to form stream (8) which enters the isomerization section C. From this, the stream (11) rich in isoamylenes is extracted and recycled to section A. Any possible $C_4^-$ or $C_6^+$ hydrocarbons formed during the isomerization are discharged through (9) and In FIG. 2 the separation section B is located after the isomerization section C.

Figure 3:
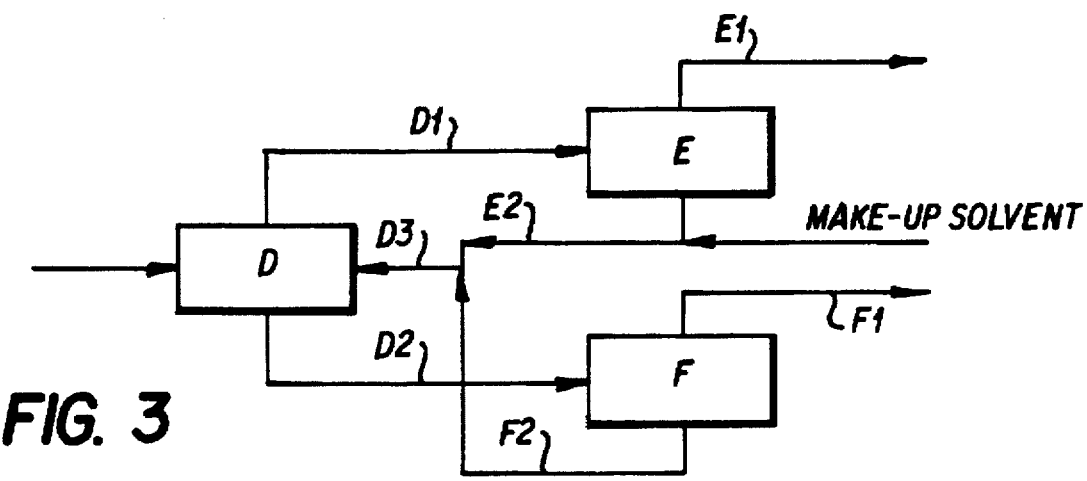

The separation section B comprises an adsorption/desorption unit D and two distillation columns E and F (FIG. 3).

To operate in continuous two units D operating alternatively, one in an adsorption phase and the other in a desorption phase, can be used.

Two streams D1 and D2 are recovered from unit D.

The stream D1, practically without olefins is recovered from the adsorption phase and is sent to the distillation column E to recover the desorbent E2, to be recycled, from the discharged pentane fraction E1.

The olefinic fraction D2 is recovered in the desorption phase and sent to the distillation column F to recover the pentene fraction F1, to be re-admitted into the cycle, from the desorbent F2 which is recycled in D.

Figure 2:
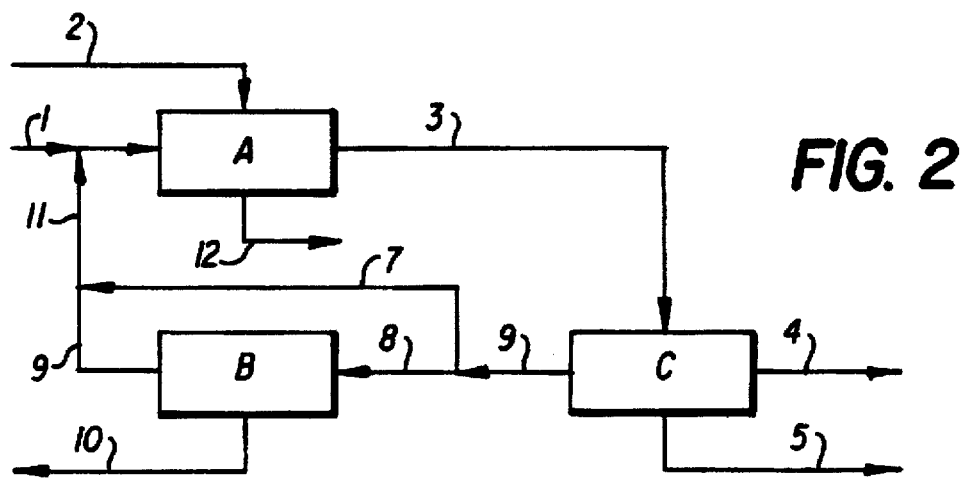

The process of the present invention, in all the illustrations of FIGS. 1 and 2, allows the discharge, in an integrated process for the production of ter-amyl alkyl ethers, of a paraffinic stream practically without olefins and consequently permits an almost integral use of the olefins available, thus maximizing the production of ter-amyl alkyl ether. It also provides a reduction in the concentration of the paraffins in the cycle and consequently reduces investments and energy consumption.

The following examples, which are illustrative but not restrictive, provide a better understanding of the present invention.

EXAMPLE 1

With reference to the scheme of FIG. 1 enclosed and relative table 1 with the process quantification for a capacity of 8.62 kg/hr of TAME, a stream of refinery $C_5$ hydrocarbon isoamylenes and other by-products generally belonging to the categories $C_{4-}$ and $C_{6+}$. These by-products are eliminated (streams 9 and 10) and the resulting fraction (8) is recycled to the TAME synthesis section.

TABLE 1

| Component | 1 | | 2 | | 3 | | 4 | |
|---|---|---|---|---|---|---|---|---|
| | Kg/hr | % w | Kg/hr | % w | Kg/hr | % w | Kg/hr | % w |
| Light Products (C4−) | 1.20 | 6.93 | | | 1.68 | 5.32 | 1.01 | 5.32 |
| Pentanes | 8.72 | 50.4S | | | 22.39 | 70.97 | 13.43 | 70.97 |
| Reactive Isoamylenes | 1.55 | 8.94 | | | 0.19 | 0.59 | 0.11 | 0.59 |
| Linear Pentenes | 3.45 | 19.96 | | | 6.95 | 22.03 | 4.17 | 22.03 |
| Heavy Products (C6+) | 2.37 | 13.72 | | | 0.34 | 1.08 | 0.20 | 1.08 |
| Water | 0.00 | 0.01 | 0.00 | 0.01 | 0.00 | 0.01 | 0.00 | 0.01 |
| TAME | 0.00 | 0.00 | | | 0.00 | 0.00 | 0.00 | 0.00 |
| Methanol | 0.00 | 0.00 | 2.04 | 99.90 | 0.00 | 0.00 | 0.00 | 0.00 |
| TOTAL | 17.29 | 100.00 | 2.04 | 100.00 | 31.55 | 100.00 | 18.93 | 100.00 |
| | 5 | | 6 | | 7 | | 8 | |
| Weight Products (C4−) | 0.67 | 5.32 | 0.10 | 1.17 | 0.91 | 8.75 | 1.58 | 6.87 |
| Pentanes | 8.96 | 70.97 | 8.06 | 94.05 | 5.37 | 51.87 | 14.33 | 62.36 |
| Reactive Isoamylenes | 0.07 | 0.59 | 0.01 | 0.08 | 0.11 | 1.01 | 0.18 | 0.78 |
| Linear Pentanes | 2.78 | 22.03 | 0.25 | 2.92 | 3.92 | 37.83 | 6.70 | 29.15 |
| Heavy Products (C6+) | 0.14 | 1.08 | 0.15 | 1.79 | 0.05 | 0.50 | 0.19 | 0.82 |
| Water | 0.00 | 0.01 | 0.00 | 0.00 | 0.00 | 0.02 | 0.00 | 0.02 |
| TAME | 0.00 | 0.00 | 0.00 | 0.00 | 0.00 | 0.00 | 0.00 | 0.00 |
| Methanol | 0.00 | 0.00 | 0.00 | 0.00 | 0.00 | 0.00 | 0.00 | 0.00 |
| TOTAL | 12.62 | 100.00 | 8.57 | 100.00 | 10.36 | 100.00 | 22.98 | 100.00 |
| | 9 | | 10 | | 11 | | 12 | |
| Weight Products (C4−) | 1.13 | 66.28 | 0.00 | 0.00 | 0.49 | 2.31 | 0.00 | 0.00 |
| Pentanes | 0.51 | 29.97 | 0.16 | 36.36 | 13.67 | 6S.60 | 0.00 | 0.02 |
| Reactive Isoamylenes | 0.02 | 1.11 | 0.04 | 9.15 | 3.11 | 14.93 | 0.00 | 0.00 |
| Linear Pentenes | 0.04 | 2.49 | 0.01 | 1.56 | 3.50 | 16.82 | 0.01 | 0.06 |
| Heavy Products (C6+) | 0.00 | 0.00 | 0.23 | 52.94 | 0.07 | 0.35 | 2.10 | 24.40 |
| Water | 0.00 | 0.25 | 0.00 | 0.00 | 0.00 | 0.00 | 0.00 | 0.00 |
| TAME | 0.00 | 0.00 | 0.00 | 0.00 | 0.00 | 0.00 | 6.51 | 75.53 |
| Methanol | 0.00 | 0.00 | 0.00 | 0.00 | 0.00 | 0.00 | 0.00 | 0.00 |
| TOTAL | 1.71 | 100.00 | 0.43 | 100.00 | 20.83 | 100.00 | 8.62 | 100.00 |

(1) having a stream rate of 17.29 kg/hr combined with the recycled stream (11) having a stream rate of 20.83 kg/hr, is fed to a TAME production reactor.

In addition, 2.04 kg/hr of methanol (line 2) are fed to the same reactor.

A production of TAME (12) is obtained of 8.51 kg/hr equal to a conversion of the reactive isoamylenes of 96%.

31.5 kg/hr of residual $C_5$ fraction containing about 71% by weight of aliphatic hydrocarbons is discharged from the synthesis reactor, through (3). About 40% of this fraction is by-passed (5) whereas the remaining portion (4) is sent to the molecular sieve separation section operating at 130° C. and 4 bars of pressure. About 30 l of zeolite X is used as adsorbent in the form of extruded pellets of 1/16" whereas n-hexane in the vapour phase (about 4 kg/hr) is used as desorbent of the adsorbed olefins. After separation by distillation of the desorbent, a stream (6) is discharged, basically consisting of 8.57 kg/hr of aliphatic hydrocarbons with an amount of paraffins of about 95%. The content of paraffinic hydrocarbons in the stream (7) is reduced to about 52% by weight, after separation by distillation of the desorbent and in the stream (8), which joins (7) and (5), the content is 62.4%.

The stream (8) is fed to the isomerization section C in which the conversion takes place of the n-pentenes to

EXAMPLE 2

With reference to FIG. 2 enclosed and relative table 2 with the process quantification for a capacity of 8.6 kg/hr of TAME, the refinery $C_5$ hydrocarbon stream (1) having a stream rate of 17.29 kg/hr combined with the recycled stream (11) having a stream rate of about 15.52 kg/hr, is fed to a TAME production reactor.

In addition, 2.02 kg/hr of methanol (line 2) are fed to the same reactor.

There is a production of TAME (12) of 8.6 kg/hr with a conversion of the reactive isoamylenes of 96%.

26.23 kg/hr of residual $C_5$ fraction containing about 66% by weight of paraffinic hydrocarbons are discharged, by (3) from the synthesis reactor A.

The stream (3) is fed to the isomerization unit C in which the conversion takes place of the n-pentenes to isoamylenes and other by-products generally belonging to the categories $C_4^-$ and $C_6^+$. These by-products are eliminated with streams (4) and (5). About 20% is by-passed (7) from the outlet stream (6), containing 69% of paraffinic hydrocarbons, whereas the remaining portion (8) is sent to the adsorption section operating at 130° C. and a pressure of 4 bars. About 30 l if zeolite X is used as adsorbent, in the form of extruded pellets of 1/16" whereas n-hexane in the vapour phase (about 4 kg/hr) is used as desorbent of the adsorbed olefins.

After separation by distillation of the desorbent, a stream (10) is discharged basically consisting of 8.29 kg/hr of aliphatic hydrocarbons with a paraffins content of about 95%. In stream (9) the content of paraffinic hydrocarbons is reduced to 48, 9% by weight, after separation by distillation of the desorbent and in stream (11), which joins (7) and (9), the content is 55%.

The composition of the $C_5$ mixture recovered at the outlet of the column is the following:

TABLE 2

| Component | 1 | | 2 | | 3 | | 4 | |
|---|---|---|---|---|---|---|---|---|
| | Kg/hr | % w | Kg/hr | % w | Kg/hr | % w | Kg/hr | % w |
| Light Products (C4–) | 1.20 | 6.93 | | | 1.66 | 6.34 | 1.19 | 62.98 |
| Pentanes | 7.2 | 50.45 | | | 17.27 | 65.92 | 0.63 | 33.16 |
| Reactive Isoamylenes | 1.55 | 8.94 | | | 0.18 | 0.70 | 0.02 | 1.13 |
| Linear Pentanes | 3.45 | 19.96 | | | 6.88 | 26.21 | 0.05 | 2.50 |
| Heavy Products (C6+) | 2.37 | 13.72 | | | 0.24 | 0.92 | 0.00 | 0.00 |
| Water | 0.00 | 0.01 | 0.00 | 0.10 | 0.00 | 0.02 | 0.00 | 0.22 |
| TAME | 0.00 | 0.00 | | | 0.00 | 0.00 | 0.00 | 0.00 |
| Methanol | 0.00 | 0.00 | 2.01 | 99.90 | 0.00 | 0.00 | 0.00 | 0.00 |
| TOTAL | 17.29 | 100.00 | 2.01 | 100.00 | 26.23 | 100.00 | 1.90 | 100.00 |
| | 5 | | 6 | | 7 | | 8 | |
| Light Products (C4–) | 0.00 | 0.00 | 0.51 | 2.12 | 0.10 | 2.12 | 0.40 | 2.12 |
| Pentanes | 0.21 | 40.92 | 16.43 | 69.00 | 3.29 | 69.00 | 13.14 | 69.00 |
| Reactive Isoamylenes | 0.04 | 7.79 | 3.19 | 13.39 | 0.64 | 13.39 | 2.55 | 13.39 |
| Linear Pentanes | 0.01 | 1.40 | 3.59 | 15.09 | 0.72 | 15.09 | 2.87 | 15.09 |
| Heavy Products (C6+) | 0.26 | 49.89 | 0.09 | 0.39 | 0.02 | 0.39 | 0.07 | 0.39 |
| Water | 0.00 | 0.00 | 0.00 | 0.00 | 0.00 | 0.00 | 0.00 | 0.00 |
| TAW | 0.00 | 0.00 | 0.00 | 0.00 | 0.00 | 0.00 | 0.00 | 0.00 |
| Methanol | 0.00 | 0.00 | 0.00 | 0.00 | 0.00 | 0.00 | 0.00 | 0.00 |
| TOTAL | 0.32 | 100.00 | 23.91 | 100.00 | 4.76 | 100.00 | 19.05 | 100.00 |
| | 9 | | 10 | | 11 | | 12 | |
| Light Products (C4–) | 0.36 | 3.37 | 0.04 | 0.50 | 0.46 | 2.99 | 0.00 | 0.00 |
| Pentanes | 5.26 | 48.85 | 7.89 | 95.17 | 8.54 | 55.03 | 0.00 | 0.01 |
| Reactive Isoamylenes | 2.41 | 22.37 | 0.14 | 1.74 | 3.05 | 19.62 | 0.00 | 0.00 |
| Pentenes | 2.71 | 25.19 | 0.16 | 1.96 | 3.43 | 22.09 | 0.01 | 0.06 |
| Heavy Products (C6+) | 0.02 | 0.21 | 0.05 | 0.63 | 0.04 | 0.27 | 2.17 | 25.26 |
| Water | 0.00 | 0.00 | 0.00 | 0.00 | 0.00 | 0.00 | 0.00 | 0.00 |
| TAME | 0.00 | 0.00 | 0.00 | 0.00 | 0.00 | 0.00 | 6.42 | 74.66 |
| Methanol | 0.00 | 0.00 | 0.00 | 0.00 | 0.00 | 0.00 | 0.00 | 0.00 |
| TOTAL | 10.76 | 100.00 | 8.29 | 100.00 | 15.52 | 100.00 | 8.60 | 100.00 |

EXAMPLE 3

Samples of type-Y zeolite in the form of pellets of 1/16" are heated in a muffle at 400° C. for 5 hours in a nitrogen stream.

4 g of zeolite thus treated are charged into an AISI 316 steel column about 25 cm long which is placed in an oven and brought to a temperature of 90° C.

When this temperature value has been reached, a vapour stream of n-hexane is passed into the tube for about 1000 seconds to saturate the active sites of the zeolite. A $C_5$ stream, in the vapour phase, is then passed with a stream rate of 0.27 cc/min.

The composition of the $C_5$ stream is the following:
weight %
i-pentane 26.52
n-pentane 33.42
3-methyl-1-butene 7.10
2-methyl-2-butene 12.91
1-pentene 20.05

The $C_5$ stream is fed to the column for a period of about 1100 seconds. The stream is then stopped and a stream of n-hexane in the vapour phase is then fed with a stream rate of about 0.36 g/min for about 1800 seconds.

The discharge effluent leaving the system is condensed in a glass exchanger.

The mixture recovered consists of the sum of the adsorbed quantities of $C_5$ stream and the quantities contained in the volume of the system not occupied by the zeolite.

| | weight % |
|---|---|
| i-pentane | 8.56 |
| n-pentane | 13.32 |
| 3-methyl-1-butene | 7.02 |
| 2-methyl-2-butene | 26.36 |
| 1-pentene | 44.74 |

The experimental data and gaschromatographic analysis of the condensed liquid show the following selectivity of the system:
i-pentane/n-pentane=0.809
3-methyl-1-butene/n-pentane=2.486
2-methyl-2-butene/n-pentane=5.13
1-pentene/n-pentane=5.60

The selectivity of the $S_i$ system refers to the ratio:

$$S_i = \frac{A_o/A_i}{R_o/R_i}$$

wherein:

A and R are, respectively, the molar fractions of the vapour fed and the recovered product;
i and o are, respectively, the general component and reference component (n-pentane).

We claim:

1. Integrated process for the production of ter-amyl alkyl ethers which comprises:
   a) feeding a $C_5$ hydrocarbon stream, basically consisting of 2-methyl-1-butene and/or 2-methyl-2-butene (reactive isoamylenes), linear pentenes, 3-methyl-1-butene and pentanes to a synthesis section of ter-amyl alkyl ethers together with a stream consisting of an aliphatic alcohol;
   b) separating the ether produced and the possible non-reacted alcohol from the hydrocarbon stream;
   c) sending the remaining hydrocarbon stream, in vapour phase, or a fraction thereof, to a separation section with molecular sieves for the separation of the pentanes from the pentenes and recovery of the pentenes;
   d) sending the hydrocarbon stream containing the recovered pentenes, together with the possible non-fed fraction in step (c), to a skeleton isomerization section for the transformation of the linear pentenes to reactive isoamylenes;
   e) recycling the isomerized stream to the synthesis reactor of the ter-amyl alkyl ether after mixing with the charge $C_5$ hydrocarbon stream.

2. Process according to claim 1, wherein the charge $C_5$ hydrocarbon stream comes from a pre-existing synthesis plant of ter-amyl alkyl ethers and is fed directly to the isomerization section.

3. Process according to claim 2, wherein the aliphatic alcohol is selected from methyl and ethyl alcohol.

4. Process according to claim 2, wherein a fraction of hydrocarbon stream of more than 5% by weight of the total stream available is sent to the absorption section.

5. Process according to claim 1, wherein the aliphatic alcohol is selected from methyl and ethyl alcohol.

6. Process according to claim 5, wherein a fraction of hydrocarbon stream of more than 5% by weight of the total stream available is sent to the absorption section.

7. Process according to claim 1, wherein a fraction of hydrocarbon stream of more than 5% by weight of the total stream available is sent to the adsorption section.

8. Process according to claim 1, wherein the molecular sieves are of the zeolitic type capable of having selectivity with respect to the double olefinic bond and selected from those having the general formula (I):

$$(Cat_{2/n}O)_x Me_2O_3(SiO_2)_y \tag{I}$$

wherein:
Cat represents a cation of valence "n", interchangeable with calcium (Ca), such as sodium, lithium, potassium, magnesium, etc;

x is a number between 0.7 and 1.5;
Me represents boron or aluminium; and
y is a number between 0.8 and 200, preferably between 1.3 and 4.

9. Process according to claim 8, wherein the molecular sieves are zeolites of the type X and Y with a particle size of between 0.1 and 3 mm.

10. Process according to claim 9, wherein the selectivity ratios olefins/paraffins of the zeolites are between 3 and 12.

11. Process according to claim 1, wherein the selectivity ratios olefins/paraffins of the zeolites are between 3 and 12.

12. Process according to claim 1, wherein the adsorption is carried out in a vapour phase at a temperature of between 20° and 180° C. and a pressure of between 1 and 10 absolute bars.

13. Process according to claim 1, wherein the recovery of the pentenes is carried out by elution of the olefins adsorbed on molecular sieves with aliphatic hydrocarbons and subsequent rectification of the mixture thus obtained.

14. Integrated process for the production of ter-amyl alkyl ethers which comprises:
   a) feeding a $C_5$ hydrocarbon stream, basically consisting of 2-methyl-1-butene and/or 2-methyl-2-butene (reactive isoamylenes), linear pentenes, 3-methyl-1-butene and pentanes to a synthesis section of ter-amyl alkyl ethers together with a stream consisting of an aliphatic alcohol;
   b) separating the ether produced and the possible non-reacted alcohol from the hydrocarbon stream;
   c) sending the remaining hydrocarbon stream to a structural skeleton isomerization section of the linear pentenes to transform the linear pentenes to reactive isoamylenes;
   d) sending the isomerized hydrocarbon stream leaving step (c), in the vapour phase, or a fraction thereof, to a molecular sieve separation section for the separation of the pentanes from the pentenes and the recovery of the pentenes;
   e) recycling the isomerized stream, containing the recovered pentenes, together with the possible fraction not fed in step (d), to the synthesis reactor of the ter-amyl alkyl ether after mixing with the charge $C_5$ hydrocarbon stream.

15. Process according to claim 14, wherein the charge $C_5$ hydrocarbon stream comes from a pre-existing synthesis plant of ter-amyl alkyl ethers and is fed directly to the isomerization section.

* * * * *